United States Patent
Riggs-Sauthier et al.

(10) Patent No.: US 8,329,958 B2
(45) Date of Patent: Dec. 11, 2012

(54) COMBINATORIAL SYNTHESIS OF PEG OLIGOMER LIBRARIES

(75) Inventors: Jennifer A. Riggs-Sauthier, Raleigh, NC (US); Nnochiri N. Ekwuribe, Cary, NC (US)

(73) Assignee: Biocon Limited (IN)

( * ) Notice: Subject to any disclaimer, the term of this patent is extended or adjusted under 35 U.S.C. 154(b) by 508 days.

(21) Appl. No.: 11/174,938

(22) Filed: Jul. 5, 2005

(65) Prior Publication Data
US 2006/0008850 A1    Jan. 12, 2006

Related U.S. Application Data

(60) Provisional application No. 60/585,182, filed on Jul. 2, 2004.

(51) Int. Cl.
*C07C 43/13* (2006.01)
*C40B 40/10* (2006.01)
(52) U.S. Cl. .......... 568/679; 506/18; 424/185.1
(58) Field of Classification Search .......... 568/679; 506/18; 424/185.1
See application file for complete search history.

(56) References Cited

U.S. PATENT DOCUMENTS

| | | | |
|---|---|---|---|
| 5,359,030 A | 10/1994 | Ekwuribe | |
| 5,438,040 A | 8/1995 | Ekwuribe | |
| 5,877,214 A * | 3/1999 | Kim | 514/571 |
| 6,191,105 B1 * | 2/2001 | Ekwuribe et al. | 514/6.5 |
| 6,309,633 B1 | 10/2001 | Ekwuribe et al. | |
| 6,380,405 B1 | 4/2002 | Ekwuribe et al. | |
| 6,638,906 B1 | 10/2003 | Ekwuribe | |
| 6,703,381 B1 | 3/2004 | Ekwuribe et al. | |
| 6,713,452 B2 | 3/2004 | Ekwuribe et al. | |
| 6,713,454 B1 | 3/2004 | Ekwuribe et al. | |
| 6,770,625 B2 | 8/2004 | Soltero et al. | |
| 6,821,529 B2 * | 11/2004 | Nelson | 424/450 |
| 6,828,297 B2 | 12/2004 | Ekwuribe et al. | |
| 6,828,305 B2 | 12/2004 | Ekwuribe et al. | |
| 6,835,802 B2 | 12/2004 | Ekwuribe et al. | |
| 6,858,580 B2 | 2/2005 | Ekwuribe et al. | |
| 6,867,183 B2 | 3/2005 | Soltero et al. | |
| 6,913,903 B2 | 7/2005 | Soltero et al. | |
| 6,930,090 B2 | 8/2005 | Ekwuribe et al. | |
| 2003/0083389 A1 * | 5/2003 | Kao et al. | 516/98 |

OTHER PUBLICATIONS

Jonstromer et al., J. Phys. Chem. 95:3293-3300 (1991).*

(Continued)

*Primary Examiner* — Ardin Marschel
*Assistant Examiner* — Jeremy C Flinders
(74) *Attorney, Agent, or Firm* — Marianne Fuierer; Moore & Van Allen, PLLC

(57) ABSTRACT

A simple chain-extending approach was established for the scale-up of the monoprotected monodisperse PEG diol materials. Reactions of THP-$(OCH_2CH_2)_n$—OMs (n=4, 8, 12) with a large excess of commercially available H—$(OCH_2CH_2)_n$—OH (n=1-4) under basic conditions led to THP-$(OCH_2CH_2)_n$—OH (n=5-15). Similarly, Me-$(OCH_2CH_2)_n$—OH (n=4-11, 13) were prepared from Me-$(OCH_2CH_2)_n$—OMs (n=3, 7, 11). For the chain elongation steps, 40-80% yields were achieved through extraction purification. PEG oligomer libraries I and II were generated in 50-95% overall yields by alkylation or acylation of THP-$(OCH_2CH_2)_n$—OH (n=1-15) followed by deprotection. Alkylation of Me-$(OCH_2CH_2)_n$—OH (n=1-11, 13) with X—$(CH_2)_m$—$CO_2R$ (X=Br or OMs) and subsequent hydrolysis led to PEG oligomer library III in 30-60% overall yields. Combinatorial purification techniques were adapted to the larger-scale library synthesis. A total of 498 compounds, each with a weight of 2-5 g and a minimum purity of 90%, were synthesized.

4 Claims, 1 Drawing Sheet

Library I (15 x 15):   $CH_3(CH_2)_m\text{-}(OCH_2CH_2)_n\text{-}OH$
(n = 1-15; m = 3-17)

Library II (15 x 11):   $CH_3(CH_2)_mCO_2\text{-}(OCH_2CH_2)_n\text{-}OH$
(n = 1-15; m = 2-8, 10, 12, 14, 16)

Library III (13 x 9):   $Me\text{-}(OCH_2CH_2)_n\text{-}O(CH_2)_mCO_2H$
(n = 1-11, 13; m = 4-7, 9-11, 14, 15)

OTHER PUBLICATIONS

Aungst et al., International Journal of Pharmaceutics, 53:227-235 (1989).*

Abstract from CAPLUS for Krishnan et al., Proceedings of the International Symposium on Controlled Release of Bioactive Materials:1038-1039 (2000).*

Abstract from CAPLUS for Liu et al., Polymer Preprints, 38(1):595-596 (1997).*

Arpicco et al., Bioconjugate Chem., 2002, 13:757-765.*

Allan, C. B.; Spreer, L. O. J. Org. Chem. 1994, 59, 7695.

An, H.; Bradshaw, J. S.; Izatt; R. M. Chem. Rev. 1992, 92, 543.

Bailey, W. F.; Zarcone, L. M. J.; Rivera, A. D. Org. Chem. 1995, 60, 2532.

Bartsch, R. A.; Cason, C. V.; Czech, B. P. J. Org. Chem. 1989, 54, 857.

Bertozzi, C. R.; Bednarski, M. D. J. Org. Chem. 1991, 56, 4326.

Boden, N.; Bushby, R. J.; Clarkson, S.; Evans, S. D.; Knowles, P. F.; Marsh, A. Tetrahedron 1997, 53, 10939.

Booth, S. Hermkens, P. H. H.; Ottenheijm, H. C. J.; Rees, D. Tetrahedron 1998, 54, 15385.

Bouzide, A.; Sauvé, G. Tetrahedron Lett. 1997, 38, 5945.

Bradshaw, J. S.; Maas, G. E.; Izatt, R. M.; Christensen; J. J. Chem. Rev. 1979, 79, 37.

Burns, C. J.; Field, L. D.; Hashimoto, K.; Petteys, B. J.; Ridley, D. D.; Sandanayake, K. R. A. S. Synth. Commun. 1999, 29, 2337.

Chen, Y.; Baker, G. L. J. Org. Chem. 1999, 64, 6870.

Coudert, G.; Mpassi, M.; Guillaumet, G.; Selve, C. Synth. Commun. 1986, 6, 19.

Deka, K.; Sarma, J. C. J. Org. Chem. 2001, 66, 1947.

Dolle, R. E. J. Comb. Chem. 2002, 4, 369. 3, 477.

Dolle, R. E. J. Comb. Chem. 2001.

Dolle, R. E.J.Comb. Chem. 2000, 2, 383.

Dolle, R. E.; Nelson, K. H., Jr. J. Comb. Chem. 1999, 3, 235.

Feldman, K.; Hauler, G.; Spencer, N. D.; Harder, P.; Grunze, M. J. Am. Chem. Soc. 1999, 121, 10134.

Garcia, J. E.; Guzman, R. Z. J. Org. Chem. 1997, 62, 8910.

Gibson, T. J. Org. Chem. 1980, 45, 1095.

Hermkens, P. H. H.; Ottenheijm, H. C. J.; Rees, D. Tetrahedron 1997, 53.

Hermkens, P. H. H.; Ottenheijm, H. C. J.; Rees, D. Tetrahedron 1996, 52, 4527-4554.

Jeong, S. W.; O'Brien, D. F. J. Org. Chem. 2001, 66, 4799.

Keegstra, E. M. D.; Zwikker, J. W.; Roest, M. R.; Jenneskens, L. W. J. Org. Chem. 1992, 57, 6678.

Leznoff, C. C. Acc. Chem. Res. 1978, 11, 327.

Maki, T.; Iwasaki, F.; Matsumura, Y. Tetrahedron Lett. 1998, 39, 5601.

Nishiguchi, T.; Fujisaki, S.; Ishii, Y.; Yano, Y.; Nishida, A. J. Org. Chem. 1994, 59, 1191.

Nishiguchi, T.; Taya, H. J. Am. Chem. Soc. 1989, 111, 9102.

Nishiguchi, T.; Fujisaki, S.; Kuroda, M.; Kajisaki, K.; Saitoh, M. J. Org. Chem. 1998, 63, 8183.

Nishiguchi, T.; Kawamine, K.; Ohtsuka, T. J. Org. Chem. 1992, 57, 312.

Pale-Grosdemange, P.; Simon, E. S.; Prime, K. L.; Whitesides, G. M. J. Am. Chem. Soc. 1998, 120, 6548.

Prime, K. L.; Whitesides, G. M. J. Am. Chem. Soc. 1993, 115, 10714.

Prime, K. L.; Whitesides, G. M. Science 1991, 252, 1164.

Ranu, B. C.; Saha, M. J. Org. Chem. 1994, 59, 8369.

Ravindranath, N; Ramesh, C.; Ramesh, C.; Das, B. Synlett 2001, 1777.

Reed, N. N.; Janda, K. D. J. Org. Chem. 2000, 65, 5843.

Renil, M.; Meldal, M. Tetrahedron Lett. 1996, 37, 6185.

Renil, M.; Nagaraj, R.; Rajasekharan, V. N. Tetrahedron 1994, 50, 6681.

Roberts, C.; Chen, C. S.; Mrksich, M.; Martichonok, V.; Ingber, D. E.; Whitesides, G. M. J. Am. Chem. Soc. 1998, 120, 6548.

Svedhem, S.; Hollander, C.-A.; Shi, J.; Konradsson, P.; Liedberg, B,; Svensson, S. C. T.J.Org. Chem. 2001, 66, 4494.

Takano, S.; Akiyama, M.; Sato, S.; Ogasawara, K. Chem. Lett. 1983, 1593.

Wilson, M. E.; Paech, K.; Zhou, W. -J.; Kurth, M. J. J. Org. Chem. 1998, 63, 5094. (b) Renil, M.; Meldal, M. Tetrahedron Lett. 1996, 37, 6185.

Zhu, P. C.; Lin, J.; Pittman, C. U., Jr. J. Org. Chem. 1995, 60, 5729.

\* cited by examiner

Library I (15 x 15): $CH_3(CH_2)_m\text{-}(OCH_2CH_2)_n\text{-}OH$
(n = 1-15; m = 3-17)

Library II (15 x 11): $CH_3(CH_2)_mCO_2\text{-}(OCH_2CH_2)_n\text{-}OH$
(n = 1-15; m = 2-8, 10, 12, 14, 16)

Library III (13 x 9): $Me\text{-}(OCH_2CH_2)_n\text{-}O(CH_2)_mCO_2H$
(n = 1-11, 13; m = 4-7, 9-11, 14, 15)

COMBINATORIAL SYNTHESIS OF PEG OLIGOMER LIBRARIES

This application claims priority to and the benefit of U.S. Provisional Patent Application No. 60/585,182 filed Jul. 2, 2004, the disclosure of which is incorporated herein by reference in its entirety.

BACKGROUND OF THE INVENTION

Combinatorial chemistry is a powerful and well-established means of generating large collections of organic molecules for drug discovery research.[1] With the dawn of the genomics and proteomics era, many of the drug discovery candidates in the future look to be protein, peptide, and perhaps, peptidomimetic based. While extremely potent as therapeutics, protein and peptide drugs are plagued with many stability issues inherent in their complex structures but most notably are their limitations with regards to oral absorption. In research efforts, we have shown that the covalent attachment of proprietary amphiphilic oligomers to protein, peptide, and even small molecule therapeutics alters the physicochemical properties of the drug molecule to overcome those challenges associated with delivery. This conjugation technology has been successfully employed to enable the oral delivery of insulin[2a-e] and calcitonin[2f] in addition to demonstrating penetration of the blood brain barrier by enkephalin.[2g] Delayed onset of action, stability to enzymatic degradation, enhanced bioactivity, and/or extended duration of action have also been observed through these modifications. To further expedite our drug-conjugate discovery process, it became necessary to possess a compound library containing a wide variety of structurally diverse amphiphilic block co-polymer oligomers. More specifically, the structural differences needed to include permutations around the number of poly(ethylene glycol) (PEG) monomers, the type and length of alkyl chain, and the lability of the drug-oligomer bond, i.e. stable or sensitive to hydrolysis or first pass effects. PEG oligomer libraries were thus designed, each bearing a hydrophilic component, a lipophilic component and a drug-attaching site. As required for our drug discovery research efforts, each library compound should have a weight of 2-5 g and a minimum purity of 90%. Usually, the scale of combinatorial library compounds is only milligrams to tens of milligrams. Construction of this type of larger-scale combinatorial libraries has been difficult and rare.

DESCRIPTION OF THE INVENTION

Library I (15×15): $CH_3(CH_2)_m\text{-}(OCH_2CH_2)_n\text{-}OH$
$(n = 1\text{-}15; m = 3\text{-}17)$ Library II (15×11): $CH_3(CH_2)_mCO_2\text{-}(OCH_2CH_2)_n\text{-}OH$
$(n = 1\text{-}15; m = 2\text{-}8, 10, 12, 14, 16)$ Library III (13×9): $Me\text{-}(OCH_2CH_2)_n\text{-}O(CH_2)_mCO_2H$
$(n = 1\text{-}11, 13; m = 4\text{-}7, 9\text{-}11, 14, 15)$ In library I, the hydrophilic and lipophilic components are connected via a nonhydrolyzable ether bond, with a hydroxyl group at the end for subsequent conjugation to the drug candidates. Exercising a different strategy in library II, the hydrophilic and lipophilic components are joined together by a hydrolyzable ester bond that cleaves once the drug-oligomer conjugate has crossed the gut epithelium into the hydrophilic environment of the bloodstream resulting in a micropegylated drug-conjugate species. Hydrolysis may be designed to occur either by changes in physiological pH or plasma enzymes. When the drug is insulin and the hydrophilic component is a PEG chain, an enhanced bioactivity was often observed.[2a] Similar to library I, library III contains nonhydrolyzable ether bond between the hydrophilic and lipophilic components; however, it was designed based on different bifunctionalization of PEG diols, the PEG and alkyl moieties were inverted from library I, and oligomer termination occurs via a carboxylic acid group for activation and subsequent drug conjugation. There are potentially 225 compounds for library I, 165 compounds for library II and 108 compounds for library III.

PEG materials have been widely used in the synthesis of crown ethers[3], surfactants, and new materials[4]. Due to increased interest in solid-phase organic synthesis, PEG materials have been frequently used in modification of polymer supports.[5] Bifunctionalization of monodisperse PEG diols, especially of large molecular weights, has been an interesting research area. Two chemically equivalent hydroxyl groups such as PEG diols are often difficult to differentiate with regards to their reactivity. Here, we report a novel and simple chain elongation strategy for the synthesis of the monofunctionalized monodisperse PEG diols (up to 15 ethylene glycol units), and the application of combinatorial techniques to the construction of the oligomer libraries.

Results and Discussion

Synthesis of $THP\text{-}(OCH_2CH_2)_n\text{-}OH$ and $Me\text{-}(OCH_2CH_2)_n\text{-}OH$ Selective monofunctionalization of symmetrical diols is important in organic synthesis and various synthetic methods have been developed for both monoacylation and monoalkylation.[6] Monobenzyl ethers of symmetrical diols were prepared by the use of a $Ag_2O$ catalyst[6a], or via diisobutylaluminum hydride cleavage of benzylidene acetals.[6b] The selective monoacylation of symmetrical diols were also achieved by the use of dimethyltin dichloride,[6c] strongly acidic ion-exchange resins,[6d] metal sulfates or hydrogen sulfates,[6e,6f] phase-transfer catalysts,[6g] inorganic polymer supports,[6h] or via cyclic compounds.[6i,6j] Instead of using these methodologies, we determined a more general and economical approach for construction of our larger-scale PEG oligomer libraries I and II was alkylation or acylation of the monoprotected PEG diols followed by deprotection.

Recently, there have been several studies on the synthesis of bifunctional monodisperse PEG derivatives (up to 14 ethylene glycol units).[7] Monofunctionalized PEG diols and monoprotected PEG diols were joined by conversion of one alcohol to a sulfonate ester or halide followed by Williamson ether synthesis. Removal of the protecting group liberated the hydroxyl group for further functionalizations. Introduction of two different protecting groups in the Williamson ether synthesis followed by selective deprotection led to the monoprotected PEG diols.[7c] Pure materials were obtained by traditional silica gel chromatography. However, our PEG oligomer libraries required a series of monoprotected PEG diols (n=1-15) at hundred gram to kilogram quantities for use as starting materials. It would be time-consuming to engage in a cycle of protecting and deprotection pathways especially for the larger molecular weight materials. A more efficient strategy requiring only one protecting group was thus developed (Scheme 1). Among the alcohol-protecting groups reported in reactions involving PEG diols,[8] we chose the THP group which could be easily introduced in the beginning stages of synthesis and cleanly removed in the final step of the process. Extraction purification procedures were also developed to avoid silica gel chromatography.

Scheme 1

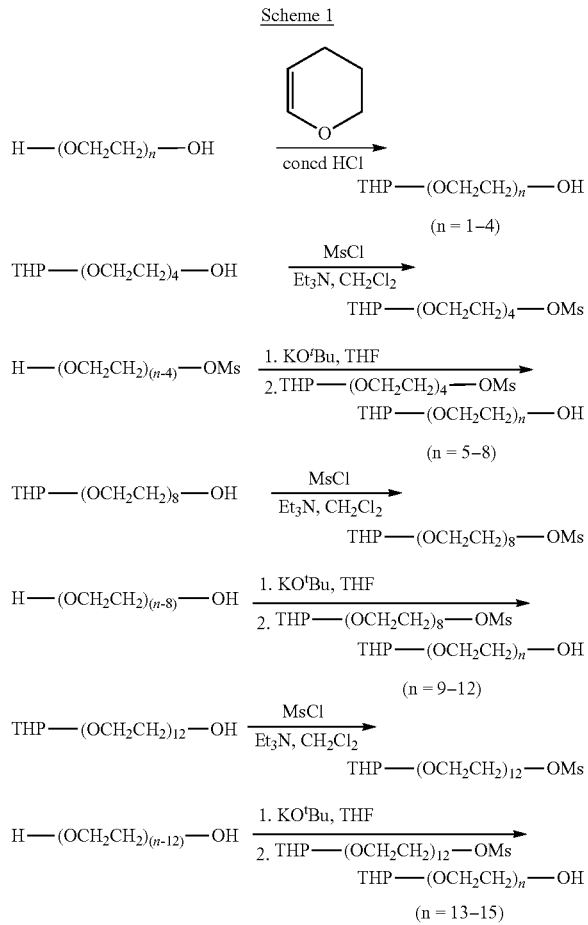

For the commercially available H—(OCH$_2$CH$_2$)$_n$—OH (n=1-4), the selective monotetrahydropyranylation can be realized by the use of catalysts such as iodine,[9a] silica chloride,[9b] ion-exchange resins,[9c] or alumina impregnated with zinc chloride.[9d] Alternatively, the mono-protected materials can be prepared by direct reactions incorporating a large excess of the inexpensive PEG diols with 3,4-dihydro-2H-pyran in the presence of a catalytic amount of conc'd HCl (Scheme 1). The latter strategy has been traditionally used in the monofunctionalization of the commercially available PEG diols.[10] The di-THP impurities were removed by dissolving the reaction mixtures in aqueous sodium bicarbonate solution followed by several ethyl acetate extractions. The desired products together with a small amount of PEG diol starting materials were recovered from the aqueous layers by dichloromethane extractions. The PEG diol impurities were further removed by extracting the dichloromethane extracts with water. The pure materials were obtained in 40-60% yields. For the synthesis of THP-(OCH$_2$CH$_2$)$_n$—OH (n=5-8), THP-(OCH$_2$CH$_2$)$_4$—OMs was prepared. Reactions of the mesylate with a large excess of H—(OCH$_2$CH$_2$)$_n$—OH (n=1-4) in the presence of KO'Bu in THF led to THP-(OCH$_2$CH$_2$)$_n$—OH (n=5-8). A larger diol/mesylate ratio was found effective to reduce the amount of the dialkylated species produced. Higher reaction temperatures were found useful to drive the alkylation reactions to completion. Similar extraction procedures gave the pure THP-(OCH$_2$CH$_2$)$_n$—OH (n=5-8). Studies have shown the elongation of PEG chain may suffer from depolymerization processes under basic conditions.[7d] We found a large excess of the PEG diols could efficiently suppress the depolymerization contamination of the products. As illustrated in Scheme 1, the chain extending approach was used repeatedly to synthesize THP-(OCH$_2$CH$_2$)$_n$—OH (n=9-15). For the alkylation steps, modest to good yields (40-80%) were achieved. An alkylation reaction carried out in a 5 L reaction flask can produce up to 350 g of the pure monoprotected PEG diol after extraction purification. Using H—(OCH$_2$CH$_2$)$_n$—OH (n=1-4), we were able to synthesize THP-(OCH$_2$CH$_2$)$_n$—OH (n=1-15) at 150-1000 g scales, which aided in the support of libraries I and II syntheses. Additionally since the THP protecting group can be cleanly removed, this simple chain elongation strategy can also be utilized for the large-scale synthesis of H—(OCH$_2$CH$_2$)$_n$—OH (n=5-15).

As shown in Scheme 2, the chain extending strategy was similarly used in the synthesis of Me-(OCH$_2$CH$_2$)$_n$—OH (n=4-15), which were required for the construction of PEG oligomer library III. In the chain elongation steps, 40-80% yields were achieved via extraction purification.

Scheme 2

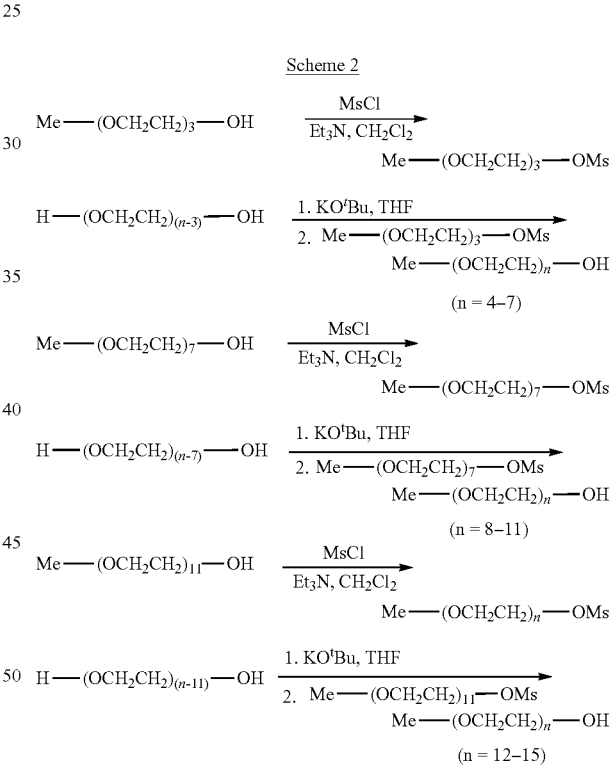

Synthesis of Library I

Gibson studied the phase-transfer synthesis of monoalkyl ethers of poly(ethylene glycols).[11] Reactions of primary alkyl chlorides (or bromides) with a slight excess of 50% aqueous sodium hydroxide and 5-10 equiv of poly(ethylene glycols) at 100° C. for 24 h provided 70-90% yields of the monoalkylated materials. This approach could be employed for the synthesis of the monoalkylated species of the commercially available poly(ethylene glycols). However, since these alkylation procedures require a high reaction temperature, we chose not to adopt this approach. Due to the easy access of mono-THP-ethers from commercially available PEG diols, a more general THP-protecting strategy was developed for the synthesis of library I (Scheme 3).

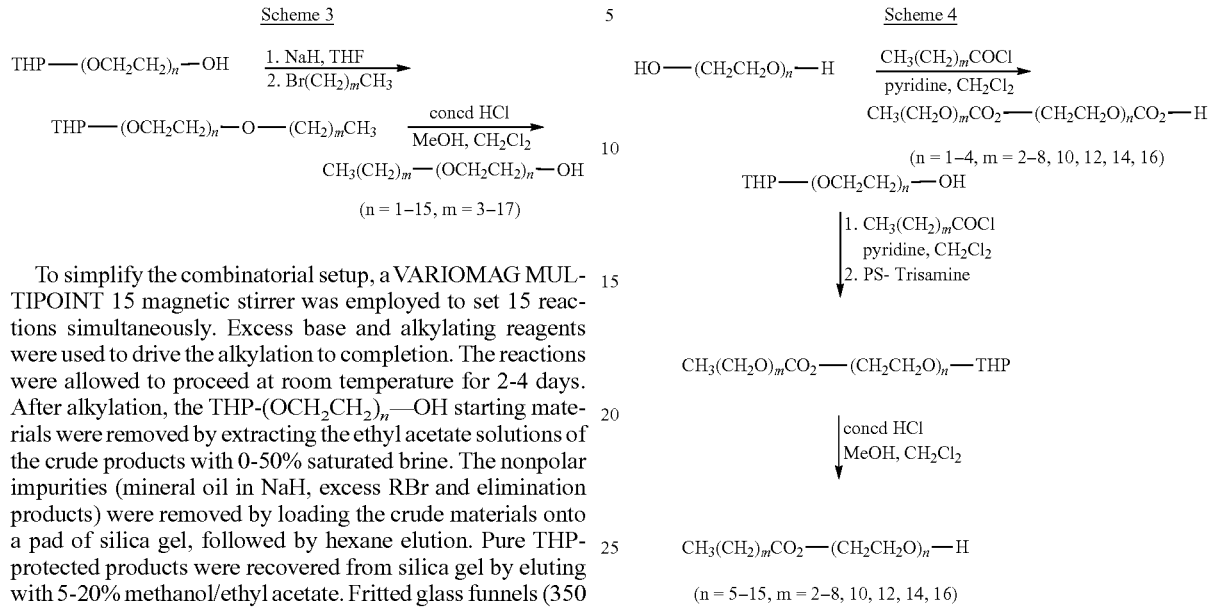

To simplify the combinatorial setup, a VARIOMAG MULTIPOINT 15 magnetic stirrer was employed to set 15 reactions simultaneously. Excess base and alkylating reagents were used to drive the alkylation to completion. The reactions were allowed to proceed at room temperature for 2-4 days. After alkylation, the THP-$(OCH_2CH_2)_n$—OH starting materials were removed by extracting the ethyl acetate solutions of the crude products with 0-50% saturated brine. The nonpolar impurities (mineral oil in NaH, excess RBr and elimination products) were removed by loading the crude materials onto a pad of silica gel, followed by hexane elution. Pure THP-protected products were recovered from silica gel by eluting with 5-20% methanol/ethyl acetate. Fritted glass funnels (350 mL) were set up for parallel silica gel purification. The resulting THP-protected intermediates were treated with conc'd HCl/MeOH/$CH_2Cl_2$ (1:50:50), and simple concentration yielded the desired pure deprotected final products. The purities of the final products were established by LC-MS (ELS) and $^1$H NMR analyses. In total, 225 compounds (15×15) were synthesized in good overall yields (50-90%) and purities (>90%).

Synthesis of Library II

Two strategies were used in the library II production (Scheme 4). Since the acylation reactions are mild and moderately clean, a synthetic route circumventing protection group strategies was adopted for the commercially available H—$(OCH_2CH_2)_n$—OH (n=1-4). In the presence of pyridine, reactions involving the addition of the diol (10 equiv) with 1 equiv of acid chlorides led to the monoacylated products. Simple aqueous extraction purification gave the desired final products in good yields (50-90%) and purities (>90%). A total of 44 final compounds (4×11) were prepared by this strategy. For H—$(OCH_2CH_2)_n$—OH (n=5-15), the THP-protecting strategy was employed for production. Following acylation, the excess acid chlorides were quenched with PS-Trisamine resin. The acid impurities generated by the hydrolysis were removed by washing the dichloromethane solutions of the crude products with 0.3 M NaOH. Pyridine was removed by azeotrope with toluene. Treatment of the resulting THP-protected intermediates with conc'd HCl/MeOH/$CH_2Cl_2$ (1:50:50) afforded the deprotected materials. To reduce the potential for transesterification contamination, the deprotection was quenched with sodium bicarbonate after 1 h. The inorganics were removed by filtration to give the pure final products in good yields (50-90%) and purities (>90%). 121 final compounds (11×11) were prepared by this strategy.

Synthesis of Library III

The first step of the library III synthesis is also alkylation (Scheme 5). However, as ester bromide or mesylate alkylating reagents were used approximately 5-15% side products due to transesterification were observed. The purification strategy employed for library I proved ineffective and silica gel chromatography became increasingly difficult. To solve this problem, a reverse transesterification step was added (Scheme 6). After alkylation, the crude products were treated with methanol and a catalytic amount of conc'd sulfuric acid. After standing overnight, the Me-$(OCH_2CH_2)_n$-esters were converted to methyl esters by releasing the Me-$(OCH_2CH_2)_n$—OH. The Me-$(OCH_2CH_2)_n$—OH starting materials were then removed by extracting the ethyl acetate solutions of the crude products with 0-50% saturated brine. The less polar methyl ester impurities were removed by loading the resulting crude products onto silica gel followed by elution with 15-35% ethyl acetate/hexane. The pure methyl ester products were recovered by elution with 10-20% methanol/dichloromethane. Upon hydrolysis, the methyl esters yielded the pure final products after subsequent acidification and dichloromethane extractions. This procedure worked more efficiently for the longer Me-$(OCH_2CH_2)_n$—OH (n>3) substrates which also were more conducive to silica gel separation. For the shorter Me-$(OCH_2CH_2)_n$—OH (n<3) substrates, purification by silica gel chromatography still proved difficult due to minimal separation, especially in a combinatorial format.

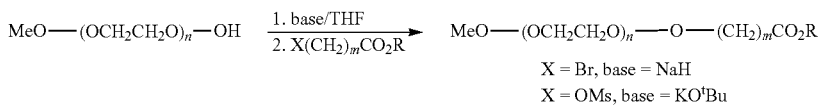

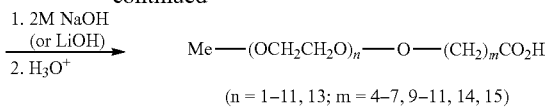

(n = 1–11, 13; m = 4–7, 9–11, 14, 15)

Scheme 6

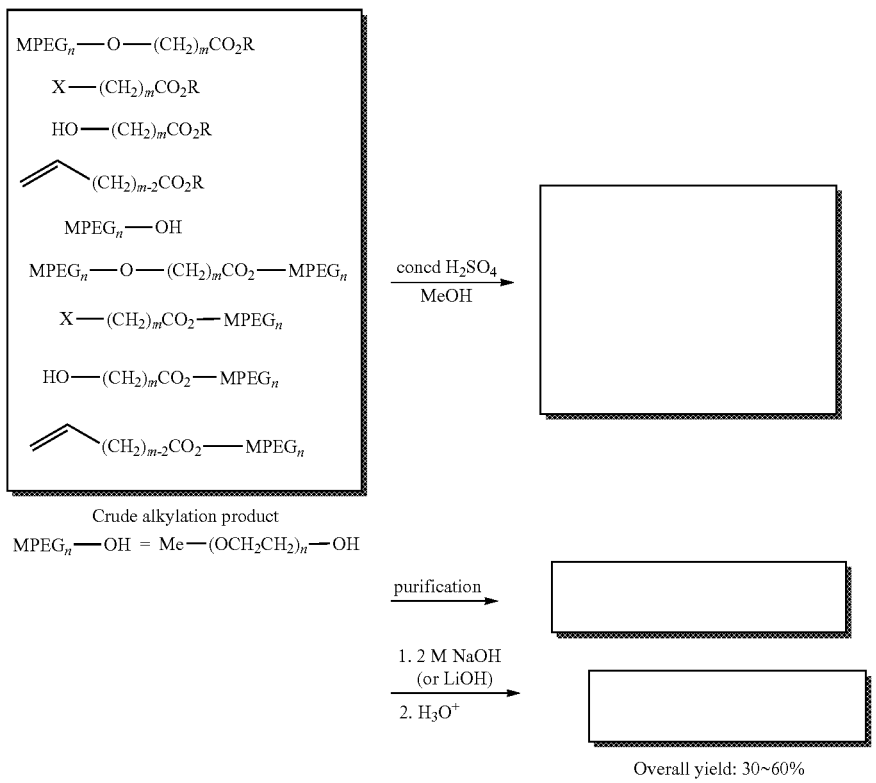

Overall yield: 30~60%

Since transesterification consumed a substantial amount of Me-(OCH$_2$CH$_2$)$_n$—OH starting materials, excess Me-(OCH$_2$CH$_2$)$_n$—OH (1.3 equiv) and base (1.4 equiv) were used to drive the alkylation to completion. A minimal amount of ester hydrolysis was observed during the aqueous work-up due to the use of excess base, predominantly in the case of the short carbon chain esters. Thus, the basic aqueous solutions were first acidified, and both the free acids and corresponding ester products were recovered by dichloromethane extractions. An advantage of the reverse transesterification process was facile conversion of the free acids to the ester products, which improved the overall yields.

For the construction of library III, 12 Me-(OCH$_2$CH$_2$)$_n$—OH (n=1-11, 13) and 9 alkylating reagents X—(CH$_2$)$_m$—CO$_2$R (m=4, 5, 6, 7, 9, 10, 11, 14, 15) were selected. Among the other 9 X—(CH$_2$)$_m$—CO$_2$R substrates, 6 bromides were commercially available and used directly in the production. The other 3 substrates were prepared as mesylates from different readily available materials (Scheme 7). For the synthesis of MsO—(CH$_2$)$_m$—CO$_2$Me (m=14, 15), the first step was conversion of the lactones to HO—(CH$_2$)$_m$—CO$_2$Me. During this process, it was not uncommon to observe 5-10% lactone starting materials after reaction completion. The crude hydroxy methyl esters (together with 5-10% lactone impurities) were directly converted to the corresponding mesylates, and the lactone impurities were easily removed by recrystallization from hexane.

Scheme 7

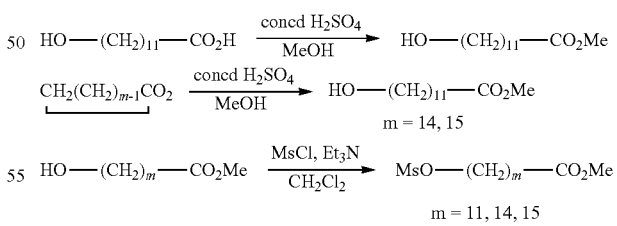

In the final hydrolysis step, 2 M NaOH was used for the shorter carbon chain substrates (m=4, 5, 6, 7, 9), and saturated LiOH (approximately 2 M) was utilized for the longer carbon chain substrates. The ester substrates were treated with 3-5 equiv of base overnight. The hydrolysis of the longer carbon chain substrates was sluggish and the reaction mixtures were monitored by LC-MS (ELS) to ensure complete hydrolysis. For those incomplete reactions, the mixtures were heated at 60° C. for a few hours to drive the hydrolysis to completion.

A total of 108 library III final compounds were synthesized in good overall yields (30-60%) and purities (>90%).

SUMMARY

A scaleable approach was developed for the preparation of monoprotected monodisperse PEG diols. THP-$(OCH_2CH_2)_n$—OH (n=5-15) and Me-$(OCH_2CH_2)_n$—OH (n=4-11, 13) were prepared by reactions of THP-$(OCH_2CH_2)_n$—OMs (n=4, 8, 12) or Me-$(OCH_2CH_2)_n$—OMs (n=3, 7, 11) with a large excess of commercially available H—$(OCH_2CH_2)_n$—OH (n=1-4) under basic conditions. For the alkylation steps, good yields (40-80%) were achieved through extraction purification. PEG oligomer libraries I and II were generated by alkylation or acylation of THP-$(OCH_2CH_2)_n$—OH (n=1-15) followed by deprotection. Alkylation of Me-$(OCH_2CH_2)_n$—OH (n=1-11, 13) with X—$(CH_2)_m$—$CO_2R$ (X=Br or OMs) and subsequent hydrolysis led to PEG oligomer library III. Combinatorial purification gave the libraries I and II in 50-95% overall yields, and the library III in 30-60% overall yields. A total of 498 compounds, each with a weight of 2-5 g and a minimal purity of 90%, were synthesized.

EXPERIMENTAL SECTION

Reagents and solvents purchased from commercial sources were used as received. VARIOMAG MULTIPOINT 15 magnetic stirrers were used for the combinatorial setup of the room temperature reactions. Proton nuclear magnetic resonance spectra were obtained on either a Bruker AC 300 NMR spectrometer at 300 MHz or a Bruker DRX 500 NMR spectrometer at 500 MHz. Tetramethylsilane was used as an internal reference. LC-MS experiments were run on a Hewlett-Packard 1100 series liquid chromatography system equipped with a SEDEX 55 evaporative light-scattering (ELS) detector and a PE SCIEX API 150 mass chromatographic analyzer. The LC conditions were as follows: a LiChrospher 100 RP-8 column (25 mm×4 mm, 5 μm) was used, and it was eluted with a gradient made up of two solvent mixtures. Solvent A consists of 5 mM aqueous ammonium acetate. Solvent B consists of 5 mM ammonium acetate in acetonitrile. The gradient was run according to the following methods: Method 1, 90:10(A/B) to 100% of B over 8 min, then 100% of B for 1 min; Method 2, 100% of A for 1 min, then 100% of A to 100% of B over 8 min. The flow rate was 1.2 mL/min. The reequilibration time between two injections was 1.5 min. All samples were injected using a Gilson 215 autosampler. The injection volume was 5 μL. The mass spectrometer was set in positive electrospray ionization modes ($ES^+$). Compound purities were assigned on the basis of ELS data.

General Procedure for the Preparation of THP-$(OCH_2CH_2)_n$—OH (n=1-4)

A solution of H—$(OCH_2CH_2)_n$—OH (2.4 mol), 3,4-dihydro-2H-pyran (54.7 mL, 0.6 mol) and 4 drops of concd HCl was stirred for 15 h at room temperature. The mixture was dissolved in 20% satd sodium bicarbonate solution (500-1000 mL), extracted with ethyl acetate (100-200 mL each time) until the di-THP impurity was removed (monitored by TLC). The aqueous layer was then saturated with sodium chloride and extracted with dichloromethane (4×200 mL). The combined organic layers were washed with water (5×100 mL), dried over anhydrous sodium sulfate, and concentrated in vacuo to give the pure product. Additional 5-10% product can be recovered from the aqueous layers by dichloromethane extractions (3×200 mL) followed by aqueous washes (5×60 mL). Yield: 40-60%.

General Procedure for the Preparation of THP-$(OCH_2CH_2)_n$—OMs (n=4, 8, 12) and Me-$(OCH_2CH_2)_n$—OMs (n=3, 7, 11)

To a stirred solution of THP-$(OCH_2CH_2)_n$—OH (or Me-$(OCH_2CH_2)_n$—OH) (0.5 mol), triethylamine (125.4 mL, 0.9 mol) in dichloromethane (500 mL) at 0° C., a solution of mesyl chloride (46.4 mL, 0.6 mol) in dichloromethane (100 mL) was added dropwise. (Attention: poor stirring and a fast addition of the mesyl chloride solution may cause the deprotection of THP-$(OCH_2CH_2)_n$—OH, which subsequently generates a mixture of THP-$(OCH_2CH_2)_n$—OTHP, THP-$(OCH_2CH_2)_n$—OMs and Ms-$(OCH_2CH_2)_n$—OMs) After the addition, the reaction was allowed to warm to room temperature and stirred for 4 h. The mixture was washed with 20% satd brine (2×500 mL), satd sodium bicarbonate solution (500 mL) and 20% satd brine (500 mL), dried over anhydrous sodium sulfate, and concentrated in vacuo to give the product. Yield: 80-99%.

General Procedure for the Preparation of THP-$(OCH_2CH_2)_{n+m}$—OH from THP-$(OCH_2CH_2)_n$—OMs (n+m=5-15), and the Preparation of Me-$(OCH_2CH_2)_{n+m}$—OH from Me-$(OCH_2CH_2)_n$—OMs (n+m=4-11, 13)

To a solution of H—$(OCH_2CH_2)_m$—OH (m=1-4, 2-5 mol) in THF (1 L) under nitrogen, potassium t-butoxide (0.55 mol) was added in 3 portions over 30 min. The reaction mixture was stirred mechanically for 1 h. A solution of THP-$(OCH_2CH_2)_n$—OMs (or Me-$(OCH_2CH_2)_n$—OMs) (0.5 mol) in THF (500 mL) was added dropwise over 30 min and the reaction was stirred at 65-70° C. for 15 h (Attention: poor stirring may cause overheating and bumping). The reaction mixture was then cooled to room temperature, filtered through a pad of Celite, washed with dichloromethane (3×200 mL) and concentrated in vacuo. The resulting oil was dissolved in 0-100% satd brine (1 L) and washed with ethyl acetate until the impurities were removed (monitored by TLC). The aqueous layer was then saturated with sodium chloride and extracted with dichloromethane (6×150 mL). The combined organic extracts were washed with water (5×100 mL), dried over anhydrous sodium sulfate, and concentrated in vacuo to give the pure product. Extra 5-10% product can be recovered from the aqueous layers by dichloromethane extractions (3×200 mL) followed by aqueous washes (5×60 mL). Yield: 40-80%.

Typical Library I Production Procedure Involving THP-$(OCH_2CH_2)_n$—OH (n=1-15) and $CH_3(CH_2)_mBr$ (m=3-17)

To a suspension of sodium hydride (56 mmol) in THF (60 mL) at 0° C. under nitrogen was added THP-$(OCH_2CH_2)_n$—OH (40 mmol) over 2-3 min. The mixture was allowed to warm to room temperature and stirred for 2 h. The alkyl bromide $CH_3(CH_2)_mBr$ (56 mmol) was added over 2-3 min and the reaction was stirred at room temperature for 2-4 days. When the reaction was completed, the solvent was removed in vacuo. The resulting residue was dissolved in ethyl acetate (400 mL), washed with 0-50% satd brine (3×50 mL), dried over anhydrous sodium sulfate and concentrated. The resulting crude material was loaded onto silica gel (200 mL). The silica gel was then washed with hexane (400 mL) followed by 5-20% methanol/ethyl acetate (600 mL) to elute the desired product. The methanol/ethyl acetate solution was concentrated in vacuo to give the THP-protected intermediate, which was subsequently dissolved in a solution of concd HCl in methanol and dichloromethane (1:50:50, 3 mL per 1 mmol of the THP-protected intermediate). After 2 h, the solvents were removed in vacuo and residual water was removed via azeotrope with toluene (100 mL) to give the final product. Yield: 50-95%.

$CH_3(CH_2)_{10}-(OCH_2CH_2)_2-OH$: $^1H$ (300 MHz, $CDCl_3$) δ 3.60-3.80 (m, 8H), 3.48 (t, 2H), 2.55 (t, 1H), 1.54-1.70 (m, 2H), 1.22-1.40 (m, 16H), 0.90 (t, 3H). MS(ESI): 261.2 $(M+H)^+$. Purity: >90% (by $^1$HNMR).

$CH_3(CH_2)_6-(OCH_2CH_2)_6-OH$: $^1H$ (300 MHz, $CDCl_3$) δ 3.58-3.78 (m, 22H), 3.45 (t, 2H), 2.79 (br s, 1H), 1.54-1.65 (m, 2H), 1.22-1.40 (m, 8H), 0.90 (t, 3H). MS(ESI): 398.6 $(M+18)^+$. Purity: >90% (by LC-MS (ELS)).

$CH_3(CH_2)_{17}-(OCH_2CH_2)_{12}-OH$: $^1H$ (300 MHz, $CDCl_3$) δ 3.55-3.80 (m, 48H), 3.45 (t, 2H), 2.62 (br s, 1H), 1.52-1.65 (m, 2H), 1.22-1.40 (m, 30H), 0.90 (t, 3H). MS(ESI): 816.6 $(M+18)^+$. Purity: >90% (by LC-MS (ELS)).

$CH_3(CH_2)_{13}-(OCH_2CH_2)_{14}-OH$: $^1H$ (300 MHz, $CDCl_3$) δ 3.55-3.78 (m, 56H), 3.45 (t, 2H), 1.52-1.65 (m, 2H), 1.20-1.35 (m, 22H), 0.90 (t, 3H). MS(ESI): 831.9 $(M+H)^+$. Purity: >90% (by LC-MS (ELS)).

$CH_3(CH_2)_{14}-(OCH_2CH_2)_{15}-OH$: $^1H$ (300 MHz, $CDCl_3$) δ 3.55-3.80 (m, 60H), 3.45 (t, 2H), 1.52-1.65 (m, 2H), 1.22-1.40 (m, 24H), 0.90 (t, 3H). MS(ESI): 906.9 $(M+18)^+$. Purity: >90% (by LC-MS (ELS)).

Typical Library II Production Procedure Involving $H-(OCH_2CH_2)_n-OH$ (n=1-4) and $CH_3(CH_2)_mCOCl$ (m=2-8, 10, 12, 14, 16)

To a stirred solution of $H-(OCH_2CH_2)_n-OH$ (100 mmol) and pyridine (20 mmol) in dichloromethane (30 mL) at 0° C. was added $CH_3(CH_2)_mCOCl$ (10 mmol). The mixture was allowed to warm to room temperature and stirred overnight. The suspension was diluted with dichloromethane (100 mL) and washed with water (100 mL), 1 M hydrochloric acid (50 mL), water (50 mL) and 1 M sodium hydroxide (50 mL). Any resulting precipitate was removed by filtration through a pad of Celite. After a final washing with water (60 mL), the organics were dried over anhydrous sodium sulfate and concentrated to give the final product. Yield: 50-95%.

$CH_3(CH_2)_{10}CO_2-(CH_2CH_2O)-H$: $^1H$ (300 MHz, $CDCl_3$) δ 4.23 (t, 2H), 3.83 (m, 2H), 2.35 (t, 2H), 2.15 (brs, 1H), 1.58-1.70 (m, 2H), 1.20-1.40 (m, 16H), 0.90 (t, 3H). MS(ESI): 245.3 $(M+H)^+$. Purity: >90% (by LC-MS (ELS)).

$CH_3(CH_2)_{16}CO_2-(CH_2CH_2O)_3-H$: $^1H$ (300 MHz, $CDCl_3$) δ 4.28 (t, 2H), 3.60-3.78 (m, 10H), 2.35 (t, 2H), 2.30 (br s, 1H), 1.58-1.70 (m, 2H), 1.20-1.40 (m, 28H), 0.90 (t, 3H). MS(ESI): 417.5 $(M+H)^+$. Purity: >90% (by LC-MS (ELS)).

Typical Library II Production Procedure Involving THP-$(OCH_2CH_2)_n-OH$ (n=5-15) and $CH_3(CH_2)_mCOCl$ (m=2-8, 10, 12, 14, 16)

To a stirred solution of THP-$(OCH_2CH_2)_n-OH$ (10 mmol) and pyridine (20 mmol) in dichloromethane (30 mL) at 0° C. was added $CH_3(CH_2)_mCOCl$ (11.5 mmol) over 2-3 min. The mixture was allowed to warm to room temperature and stirred overnight. PS-Trisamine resin (4.5 mmol) was added and the reaction mixture was stirred for another 2 h. The resin was removed by filtration and washed with dichloromethane (2×30 mL). The combined organics were washed with water (60 mL) and 0.3 M sodium hydroxide (60 mL). Any resulting precipitate was removed by filtration through a pad of Celite. After a final washing with water (60 mL), the organics were dried over anhydrous sodium sulfate, filtered through silica gel (70 mL), and further eluted with 1-10% methanol/ethyl acetate (400 mL). The combined filtrates were concentrated in vacuo. To the resultant residue, toluene (100 mL) was added, and the solution was again concentrated in vacuo to give the THP-protected intermediate that was free of residual pyridine. The resulting material was then dissolved in a solution of concd hydrochloric acid in methanol and dichloromethane (1:50:50, 3 mL per 1 mmol of the THP-protected intermediate). After approximately 1 h, the reaction was quenched with sodium bicarbonate (5 equiv) and the solvents were removed in vacuo. To the residue was added dichloromethane (100 mL) and the resulting mixture was dried over anhydrous sodium sulfate, and concentrated in vacuo to give the final product. Yield: 50-95%.

$CH_3(CH_2)_2CO_2-(CH_2CH_2O)_5-H$: $^1H$ (300 MHz, $CDCl_3$) δ 4.20 (t, 2H), 3.54-3.70 (m, 26H), 3.0 (br s, 1H), 2.28 (t, 2H), 1.55-1.70 (m, 2H), 0.90 (t, 3H). MS(ESI): 309.5 $(M+H)^+$. Purity: >90% (by LC-MS (ELS)).

$CH_3(CH_2)_2CO_2-(CH_2CH_2O)_7-H$: $^1H$ (300 MHz, $CDCl_3$) δ 4.22 (t, 2H), 3.60-3.78 (m, 26H), 2.35 (t, 2H), 1.58-1.72 (m, 2H), 0.96 (t, 3H). MS(ESI): 397.1 $(M+H)^+$. Purity: >90% (by LC-MS (ELS)).

$CH_3(CH_2)_{14}CO_2-(CH_2CH_2O)_7-H$: $^1H$ (300 MHz, $CDCl_3$) δ 4.22 (t, 2H), 3.60-3.78 (m, 26H), 2.33 (t, 2H), 1.58-1.70 (m, 2H), 1.18-1.38 (m, 24H), 0.90 (t, 3H). MS(ESI): 565.5 $(M+H)^+$. Purity: >90% (by LC-MS (ELS)).

$CH_3(CH_2)_{12}CO_2-(CH_2CH_2O)_{14}-H$: $^1H$ (300 MHz, $CDCl_3$) δ 4.22 (t, 2H), 3.60-3.78 (m, 54H), 2.33 (t, 2H), 1.55-1.65 (m, 2H), 1.20-1.38 (m, 20H), 0.88 (t, 3H). MS(ESI): 845.7 $(M+H)^+$. Purity: >90% (by LC-MS (ELS)).

$CH_3(CH_2)_{16}CO_2-(CH_2CH_2O)_{15}-H$: $^1H$ (300 MHz, $CDCl_3$) δ 4.22 (t, 2H), 3.60-3.80 (m, 58H), 2.35 (t, 2H), 1.58-1.72 (m, 2H), 1.20-1.40 (m, 28H), 0.90 (t, 3H). MS(ESI): 963.0 $(M+18)^+$. Purity: >90% (by LC-MS (ELS)).

Preparation of $HO-(CH_2)_{11}-CO_2Me$

A suspension of $HO-(CH_2)_{11}-CO_2H$ (45 g, 0.21 mol) and concd sulfuric acid (1 mL) in methanol (1 L) was stirred at room temperature for 3 days. Sodium bicarbonate (8.4 g, 0.1 mol) was then added and the mixture was concentrated by rotary evaporation. To the resulting crude was added dichloromethane (50 mL). The solution was filtered through 150 ml silica gel, and the silica gel was further eluted with dichloromethane (500 mL). The combined organics were concentrated by rotary evaporation to give 46 g (96%) of the title compound.

General Procedure for the Preparation of $HO-(CH_2)_m-CO_2Me$ (m=14, 15)

A solution of the lactone starting material (0.25 mol) and concd sulfuric acid (1 mL) in methanol (1 L) was stirred at room temperature for 3 days. Sodium bicarbonate (8.4 g, 0.1 mol) was then added and the mixture was concentrated by rotary evaporation. To the resulting crude was added dichloromethane (50 mL). The mixture was filtered through 150 ml silica gel, and the silica gel was further eluted with dichloromethane (500 mL). The combined organics were concentrated by rotary evaporation to give the product, which was found to contain 5-10% of the lactone starting material. This crude material was used in the next step without further purification. Crude yield: >90%.

General Procedure for the Preparation of $MsO-(CH_2)_m-CO_2Me$ (m=11, 14, 15)

To a stirred solution of $HO-(CH_2)_m-CO_2Me$ (0.2 mol) and triethylamine (41.8 mL, 0.3 mol) in dichloromethane (600 mL) at 0° C., a solution of mesyl chloride (18.6 μL, 0.24 mol) in dichloromethane (50 mL) was added dropwise. After the addition, the mixture was allowed to warm to room temperature and stirred overnight. The crude was washed with water, satd sodium bicarbonate solution and brine, dried over anhydrous sodium sulfate, and concentrated in vacuo to give the product. When m=14 and 15, the pure materials were obtained by recrystallization from hexane. Yield: >90%.

m=11, light yellow solid. $^1$H (300 MHz, CDCl$_3$) δ 4.22 (t, 2H), 3.67 (s, 3H), 3.01 (s, 3H), 2.30 (t, 3H), 1.70-1.80 (m, 2H), 1.68-1.70 (m, 2H), 1.28-1.50 (m, 14H).

m=14, white solid. $^1$H (300 MHz, CDCl$_3$) δ 4.23 (t, 2H), 3.67 (s, 3H), 3.01 (s, 3H), 2.31 (t, 3H), 1.72-1.82 (m, 2H), 1.57-1.72 (m, 2H), 1.24-1.48 (m, 20H).

m=15, white solid. $^1$H (300 MHz, CDCl$_3$) δ 4.22 (t, 2H), 3.67 (s, 3H), 3.01 (s, 3H), 2.30 (t, 3H), 1.71-1.81 (m, 2H), 1.58-1.71 (m, 2H), 1.20-1.48 (m, 22H).

Typical Library III Production Procedure Involving Me-(OCH$_2$CH$_2$)$_n$—OH (n=1-11, 13) and Br—(CH$_2$)$_m$—CO$_2$R (m=4-7, 9, 10) [or MsO—(CH$_2$)$_m$—CO$_2$Me (m=11, 14, 15)]

To a suspension of sodium hydride (or potassium t-butoxide) (56 mmol) in THF (80 mL) at 0° C. under nitrogen was added Me-(OCH$_2$CH$_2$)$_n$—OH (52 mmol) over 2-3 min. The mixture was allowed to warm to room temperature and stirred for 2 h. The bromo-ester Br—(CH$_2$)$_m$—CO$_2$R (or MsO—(CH$_2$)$_m$—CO$_2$R) (40 mmol) was added over 2-3 min, and the reaction was stirred at room temperature for 2-4 days. The solvent was removed in vacuo and the crude was taken up in water (25 mL). The mixture was acidified with concd hydrochloric acid to pH 3-5, saturated with sodium chloride and extracted with dichloromethane (3×50 mL). The combined extracts were washed with satd brine (20 mL), dried over anhydrous sodium sulfate, and concentrated in vacuo. The resulting residue was treated with methanol (200 mL) and a catalytic amount of concd sulfuric acid (0.5 mL). After 24 h, sodium bicarbonate (5 g) was added to neutralize the sulfuric acid and the mixture was concentrated in vacuo. To the resultant residue was added ethyl acetate (400 mL) and the mixture was washed with 0-50% satd brine (3×50 mL), dried over anhydrous sodium sulfate, and concentrated in vacuo to give the crude methyl ester. The crude ester was then loaded onto silica gel (200 mL), and washed with 15-35% ethyl acetate/hexane followed by 10-20% methanol/dichloromethane to elute the desired product. The pure methyl ester was treated with 2 M sodium hydroxide (or satd lithium hydroxide) (4 equiv) at room temperature for 24-48 h and the reaction was monitored by LC-MS (ELS). If the reaction was incomplete, the mixture was heated at 60° C. for a few hours to drive the hydrolysis to completion. The reaction mixture was then cooled to room temperature and acidified with concd hydrochloric acid to pH 3-5. The acidic aqueous mixture was saturated with sodium chloride and extracted with dichloromethane (5×50 mL). The combined extracts were dried over anhydrous sodium sulfate and concentrated in vacuo to give the final product. Yield: 30-60%.

Me-(OCH$_2$CH$_2$)—O(CH$_2$)$_4$CO$_2$H: $^1$H (500 MHz, CDCl$_3$) δ 3.46-3.67 (m, 6H), 3.38 (s, 3H), 2.40 (t, 2H), 1.65-1.78 (m, 4H). Purity: >90% (by $^1$H NMR).

Me-(OCH$_2$CH$_2$)$_5$—O(CH$_2$)$_7$CO$_2$H: $^1$H (500 MHz, CDCl$_3$) δ 3.40-3.70 (m, 22H), 3.38 (s, 3H), 2.33 (t, 2H), 1.55-1.70 (m, 4H), 1.30-1.40 (m, 6H). MS(ESI): 412.4 (M+18)$^+$. Purity: >90% (by LC-MS (ELS)).

Me-(OCH$_2$CH$_2$)$_9$—O(CH$_2$)$_7$CO$_2$H: $^1$H (300 MHz, CDCl$_3$) δ 3.40-3.70 (m, 38H), 3.38 (s, 3H), 2.33 (t, 2H), 1.50-1.70 (m, 4H), 1.28-1.40 (m, 6H). MS(ESI): 598.8 (M+18)$^+$. Purity: >90% (by LC-MS (ELS)).

Me-(OCH$_2$CH$_2$)$_9$—O(CH$_2$)$_{11}$CO$_2$H: $^1$H (300 MHz, CDCl$_3$) δ 3.40-3.70 (m, 38H), 3.38 (s, 3H), 2.33 (t, 2H), 1.50-1.70 (m, 4H), 1.28-1.40 (m, 14H). MS(ESI): 644.6 (M+18)$^+$. Purity: >90% (by LC-MS (ELS)).

Me-(OCH$_2$CH$_2$)$_{10}$—O(CH$_2$)$_6$CO$_2$H: $^1$H (300 MHz, CDCl$_3$) δ 3.40-3.70 (m, 42H), 3.38 (s, 3H), 2.33 (t, 2H), 1.50-1.70 (m, 4H), 1.32-1.42 (m, 4H). MS(ESI): 618.5 (M+18)$^+$. Purity: >90% (by LC-MS (ELS)).

Me-(OCH$_2$CH$_2$)$_{13}$—O(CH$_2$)$_4$CO$_2$H: $^1$H (300 MHz, CDCl$_3$) δ 3.45-3.70 (m, 54H), 3.38 (s, 3H), 2.35 (t, 2H), 1.55-1.77 (m, 4H), 1.28-1.40 (m, 6H). MS(ESI): 722.7 (M+18)$^+$. Purity: >90% (by LC-MS (ELS)).

Me-(OCH$_2$CH$_2$)$_{13}$—O(CH$_2$)$_5$CO$_2$H: $^1$H (300 MHz, CDCl$_3$) δ 3.42-3.70 (m, 54H), 3.38 (s, 3H), 2.33 (t, 2H), 1.55-1.72 (m, 4H), 1.35-1.50 (m, 2H). MS(ESI): 736.8 (M+18)$^+$. Purity: >90% (by LC-MS (ELS)).

Me-(OCH$_2$CH$_2$)$_{13}$—O(CH$_2$)$_7$CO$_2$H: $^1$H (300 MHz, CDCl$_3$) δ 3.40-3.70 (m, 54H), 3.38 (s, 3H), 2.33 (t, 2H), 1.50-1.70 (m, 4H), 1.28-1.40 (m, 6H). MS(ESI): 764.4 (M+18)$^+$. Purity: >90% (by LC-MS (ELS)).

Me-(OCH$_2$CH$_2$)$_{13}$—O(CH$_2$)$_{10}$CO$_2$H: $^1$H (300 MHz, CDCl$_3$) δ 3.40-3.70 (m, 54H), 3.38 (s, 3H), 2.33 (t, 2H), 1.50-1.70 (m, 4H), 1.23-1.40 (m, 12H). MS(ESI): 806.7 (M+18)$^+$. Purity: >90% (by LC-MS (ELS)).

Me-(OCH$_2$CH$_2$)$_{13}$—O(CH$_2$)$_{14}$CO$_2$H: $^1$H (300 MHz, CDCl$_3$) δ 3.40-3.70 (m, 54H), 3.38 (s, 3H), 2.33 (t, 2H), 1.50-1.70 (m, 4H), 1.20-1.40 (m, 20H). MS(ESI): 863.7 (M+18)$^+$. Purity: >90% (by LC-MS (ELS)).

Me-(OCH$_2$CH$_2$)$_{13}$—O(CH$_2$)$_{15}$CO$_2$H: $^1$H (300 MHz, CDCl$_3$) δ 3.40-3.70 (m, 54H), 3.38 (s, 3H), 2.33 (t, 2H), 1.50-1.70 (m, 4H), 1.20-1.40 (m, 22H). MS(ESI): 876.6 (M+18)$^+$. Purity: >90% (by LC-MS (ELS)).

References

[1] (a) Dolle, R. E. *J. Comb. Chem.* 2002, 4, 369. (b) Dolle, R. E. *J. Comb. Chem.* 2001, 3, 477. (c) Dolle, R. E. *J. Comb. Chem.* 2000, 2, 383. (d) Dolle, R. E.; Nelson, K. H., Jr. *J. Comb. Chem.* 1999, 3, 235. (e) Booth, S. Hermkens, P. H. H.; Ottenheijm, H. C. J.; Rees, D. *Tetrahedron* 1998, 54, 15385. (f) Hermkens, P. H. H.; Ottenheijm, H. C. J.; Rees, D. *Tetrahedron* 1997, 53, 5647. (g) Hermkens, P. H. H.; Ottenheijm, H. C. J.; Rees, D. *Tetrahedron* 1996, 52, 4527-4554.

[2] (a) Ekwuribe, N.; Ramaswamy, M.; Rajagopalan, J. S. U.S. Pat. No. 6,309,633, 2001. (b) Ekwuribe, N.; Ramaswamy, M.; Radhakrishnan, B.; Allaudeen, H. S. U.S. Pat. No. 6,191,105, 2001. (c) Ekwuribe, N. U.S. Pat. No. 5,681,811, 1997. (d) Ekwuribe, N. N.; Mich, S. U.S. Pat. No. 5,438,040, 1995. (e) Ekwuribe, N.; Price, C.; Ansari, A.; Odenbaugh, A. U.S. Pat. No. 6,713,452, 2004. (g) Ekwuribe, N. N; Mich, S. U.S. Pat. No. 5,359,030, 1994. (f) Ekwuribe, N.; Radhakrishnan, B.; Price, C.; Anderson, W.; Ansari, A.; U.S. Pat. No. 6,703,381, 2004.

[3] (a) An, H.; Bradshaw, J. S.; Izatt; R. M. *Chem. Rev.* 1992, 92, 543. (b) Bradshaw, J. S.; Maas, G. E.; Izatt, R. M.; Christensen; J. J. *Chem. Rev.* 1979, 79, 37.

[4] (a) Feldman, K.; Hähner, G.; Spencer, N. D.; Harder, P.; Grunze, M. *J. Am. Chem. Soc.* 1999, 121, 10134. (b) Roberts, C.; Chen, C. S.; Mrksich, M.; Martichonok, V.; Ingber, D. E.; Whitesides, G. M. *J. Am. Chem. Soc.* 1998, 120, 6548. (c) Prime, K. L.; Whitesides, G. M. *J. Am. Chem. Soc.* 1993, 115, 10714. (d) Prime, K. L.; Whitesides, G. M. *Science* 1991, 252, 1164.

[5] (a) Wilson, M. E.; Paech, K.; Zhou, W.-J.; Kurth, M. J. *J. Org. Chem.* 1998, 63, 5094. (b) Renil, M.; Meldal, M. *Tetrahedron Lett.* 1996, 37, 6185. (c) Renil, M.; Nagaraj, R.; Rajasekharan, V. N. *Tetrahedron* 1994, 50, 6681.

[6] (a) Bouzide, A.; Sauvé, G. *Tetrahedron Lett.* 1997, 38, 5945. (b) Takano, S.; Akiyama, M.; Sato, S.; Ogasawara, K. *Chem. Lett.* 1983, 1593. (c) Maki, T.; Iwasaki, F.; Matsumura, Y. *Tetrahedron Lett.* 1998, 39, 5601. (d) Nishiguchi, T.; Fujisaki, S.; Ishii, Y.; Yano, Y.; Nishida, A. *J. Org. Chem.* 1994, 59, 1191. (e) Nishiguchi, T.; Taya, H. *J. Am. Chem. Soc.* 1989, 111, 9102. (f) Nishiguchi, T.; Kawamine, K.; Ohtsuka, T. *J. Org. Chem.* 1992, 57, 312. (g) Zerda, J. D. L.; Barak, G.; Saason, Y. *Tetrahedron Lett.* 1989, 29, 1533. (h) Leznoff, C. C. *Acc. Chem. Res.* 1978, 11, 327. (i) Zhu, P. C.; Lin, J.; Pittman, C. U., Jr. *J. Org. Chem.* 1995, 60, 5729. (j) Bailey, W. F.; Zarcone, L. M. J.; Rivera, A. D. *J. Org. Chem.* 1995, 60, 2532.

[7] (a) Svedhem, S.; Hollander, C.-Å.; Shi, J.; Konradsson, P.; Liedberg, B,; Svensson, S. C. T. *J. Org. Chem.* 2001, 66, 4494. (b) Chen, Y.; Baker, G. L. *J. Org. Chem.* 1999, 64, 6870. (c) Burns, C. J.; Field, L. D.; Hashimoto, K.; Petteys, B. J.; Ridley, D. D.; Sandanayake, K. R. A. S. *Synth. Commun.* 1999, 29, 2337. (d) Boden, N.; Bushby, R. J.; Clarkson, S.; Evans, S. D.; Knowles, P. F.; Marsh, A. *Tetrahedron* 1997, 53, 10939.

[8] (a) Reed, N. N.; Janda, K. D. *J. Org. Chem.* 2000, 65, 5843. (b) Garcia, J. E.; Guzmán, R. Z. *J. Org. Chem.* 1997, 62, 8910. (c) Allan, C. B.; Spreer, L. O. *J. Org. Chem.* 1994, 59, 7695. (d) Coudert, G.; Mpassi, M.; Guillaumet, G.; Selve, C. *Synth. Commun.* 1986, 6, 19. (e) Keegstra, E. M. D.; Zwikker, J. W.; Roest, M. R.; Jenneskens, L. W. *J. Org. Chem.* 1992, 57, 6678. (f) Bartsch, R. A.; Cason, C. V.; Czech, B. P. *J. Org. Chem.* 1989, 54, 857.

[9] (a) Deka, K.; Sarma, J. C. *J. Org. Chem.* 2001, 66, 1947. (b) Ravindranath, N; Ramesh, C.; Ramesh, C.; Das, B. *Synlett* 2001, 1777. (c) Nishiguchi, T.; Fujisaki, S.; Kuroda, M.; Kajisaki, K.; Saitoh, M. *J. Org. Chem.* 1998, 63, 8183. (d) Ranu, B. C.; Saha, M. *J. Org. Chem.* 1994, 59, 8369.

[10] (a) Jeong, S. W.; O'Brien, D. F. *J. Org. Chem.* 2001, 66, 4799. (b) Pale-Grosdemange, P.; Simon, E. S.; Prime, K. L.; Whitesides, G. M. *J. Am. Chem. Soc.* 1998, 120, 6548. (c) Bertozzi, C. R.; Bednarski, M. D. *J. Org. Chem.* 1991, 56, 4326. (d) Nakatsuji, Y.; Kameda, N.; Okahara, M. *Synthesis* 1987, 281.

[11] Gibson, T. *J. Org. Chem.* 1980, 45, 1095.

We claim:

1. A PEG oligomer combinatorial library consisting of three different groups of compounds having structurally diverse amphiphilic block co-polymer oligomers with permutations of number of poly(ethylene glycol) (PEG) monomers and alkyl chains and a conjugation site for binding with a testing drug candidate, the groups consisting of:

(a) a first group of oligomers consisting of two or more oligomers having the formula $CH_3(CH_2)_m—(OCH_2CH_2)_n—OH$ wherein m is 3-17 and n is 1-15, wherein hydrophilic and lipophilic components are connected via a nonhydrolyzable ether bond and a hydroxyl group for subsequent conjugation to the testing drug candidate;

(b) a second group of oligomers consisting of two or more oligomers having the formula $CH_3(CH_2)_{m'}—C(O)O—(CH_2CH_2O)_{n'}—H$ wherein m' is 2-8, 10, 12, 14, and 16 and n' is 1-15, wherein hydrophilic and lipophilic components are joined together by a hydrolyzable ester bond and a hydroxyl group for subsequent conjugation to the testing drug candidate; and (c) a third group of oligomers consisting of two or more oligomers having the formula $CH_3(OCH_2CH_2)_{n''}—O—(CH_2)_{m''}CO_2H$ wherein m" is 4-7, 9-11, 14, and 15 and n" is 1-11, and 13 wherein hydrophilic and lipophilic components are connected via a nonhydrolyzable ether bond and the hydrophilic and lipophilic components are inverted relative to the first group and a carboxylic acid group for subsequent conjugation to the testing drug candidate;

and wherein each compound has a weight of from 2-5 grams and a minimum purity of 90% to provide three different groups for the combinational library for drug discovery.

2. The oligomer library of claim 1 wherein the first group consists of 225 compounds.

3. The oligomer library of claim 1, wherein the second group consists of 165 compounds.

4. The oligomer library of claim 1, wherein the third group consists of 108 compounds.

* * * * *